Figure 1:
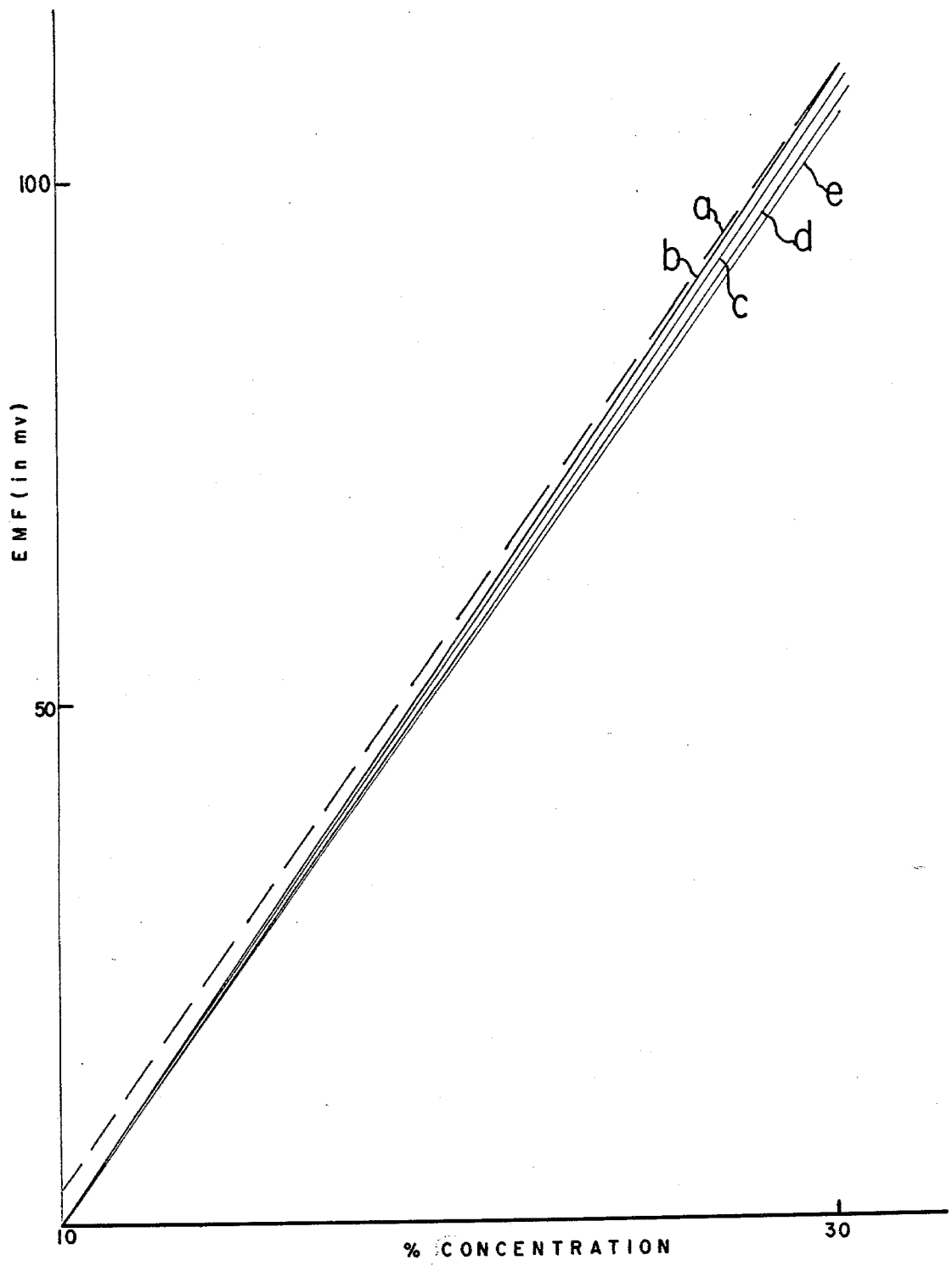

United States Patent [19]

Spaziante et al.

[11] 4,262,252
[45] Apr. 14, 1981

[54] MEASURING ELECTRODE FOR SULFURIC ACID CONCENTRATION

[75] Inventors: Placido M. Spaziante, Lugano, Switzerland; Luigi Giuffre; Giovanni Modica, both of Milan, Italy

[73] Assignee: Panclor S.A., Taverne, Switzerland

[21] Appl. No.: 908,266

[22] Filed: May 22, 1978

[30] Foreign Application Priority Data

Jun. 13, 1977 [CH] Switzerland .......................... 7267/77

[51] Int. Cl.³ ............................................ G01N 27/42
[52] U.S. Cl. .................................. 324/425; 204/195 F
[58] Field of Search ...................... 324/29, 29.5, 30 R, 324/30 B, 425, 426, 432; 204/195 F, 2.1

[56] References Cited

U.S. PATENT DOCUMENTS

| 3,060,374 | 10/1962 | Strain | 324/29.5 |
|---|---|---|---|
| 3,060,375 | 10/1962 | Godshalk et al. | 324/29.5 |
| 3,331,021 | 7/1967 | Marsh et al. | 324/29.5 |
| 3,810,828 | 5/1974 | Lindholm | 204/195 F |
| 3,929,505 | 12/1975 | Burkett | 204/2.1 |
| 4,140,589 | 2/1979 | Hradcovsky | 204/2.1 |

Primary Examiner—Michael J. Tokar
Attorney, Agent, or Firm—Hammond & Littell, Weissenberger and Muserlian

[57] ABSTRACT

A measuring electrode for determining the concentration of aqueous sulfuric acid solutions comprising a lead electrode activated by anodic polarization in aqueous sulfuric acid and a process of determining the state of charge of a lead-acid battery.

7 Claims, 2 Drawing Figures

MEASURING ELECTRODE FOR SULFURIC ACID CONCENTRATION

STATE OF THE ART

Determination of the concentration of a sulfuric acid solution can be effected either directly or indirectly. The indirect method consists essentially of volumetric, potentiometric, conductometric and, wherever possible, of weight titrations which are the most used methods for an indirect determination of the strength thereof. These methods are reliable but disadvantageous when an immediate determination of the strength of the solution is needed and they involve the loss of the sample of the solution. Furthermore, these indirect methods can be applied only to dilute solutions and when a strength determination of a concentrated sulfuric acid solution is required, sampling and dilution of the sample must be effected.

The direct methods, i.e. instant determination, of determining the strength of sulfuric acid consists in the measurement of some physical properties of the solution and particularly the electrical conductivity, the density or the potential exhibited by an indicator or measuring electrode sensitive to the ionic species whose concentration has to be determined connected to a reference electrode with a known constant potential, that is the setting up of a galvanic cell wherein the open circuit potential is proportional to the concentration of the relevant ionic species. For some applications, substances whose color changes according to the solution pH are employed for a colorimetric determination of the strength.

The methods other than the colorimetric method have the advantage that they do not alter the solution but they are not of common use. Conductimetric strength determinations are reliable ony in the case of solutions constituted by a single electrolyte. The method cannot be applied to solutions comprising more than one electrolyte wherein all the ionic species would contribute to the measured conductivity value. The use of the density meters is limited for the same reasons. The potentiometric method utilizing measuring electrodes selectively sensitive to the particular ionic species overcomes the disadvantages of the other methods.

Therefore, there is a need for highly selective measuring electrodes which are sensitive over a large range of concentration. To determine the concentration of sulfuric acid over a large concentration range, the measuring electrode must be reversibly sensitive to the more unstable species present in the system and must be chemically resistant for a long period of time to the acid or basic environment. Particularly, it is of great practical interest to determine sulfuric acid concentrations instantaneously and continuously in the range of concentrations from 10 to 30% which is the range of concentration found in lead-acid batteries used for the reversible storage of energy.

Considering the discharging voltage characteristics of a lead-acid battery, it is evident that the voltage determination cannot give a reliable indication of the charge condition of the battery since even near full discharge the voltage is almost the same as that of a fully charged battery. A reliable method to assess the charge condition is to measure the sulfuric acid concentration. Results of conductivity determination are not reliable due to the presence of impurities and the density determination while reliable entails a bothersome manual inspection and is not easily automatized. Therefore, the determination of the state of charge of a lead-acid battery can be effected potentionmetrically by a measuring electrode sensitive to the anion at least up to acid concentrations of 30 to 40%.

In the case of sulfuric acid solutions, the sulfuric acid contained in the solution dissociates according to the following equations:

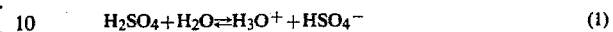

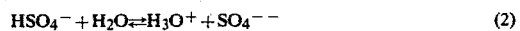

with the concentration of the anions $HSO_4^-$ and $SO_4^{--}$ depending on the acid concentration. In sulfuric acid concentrations from 10 to 80%, practically only the ions coming from reaction 1 are present in the solution and it has been ascertained that in this concentration range, the most mobile species is the anion $HSO_4^-$ which is 2 to 3 times more mobile than the proton. Practically, the determination of the strength of the sulfuric acid in this concentration range is limited to the determination of the anion $HSO_4^-$.

Therefore, for the potentiometric determination of a sulfuric acid strength higher than 1 N, it is necessary to provide a measuring electrode sensitive, in a reversible way, only to the $HSO_4^-$ anion together with a reference electrode having a known fixed potential. The cell constituted by these two electrodes must be uneffected by aqueous sulfuric acid in which it operates continuously. The measuring electrode reversibly sensitive to variations of $HSO_4^-$ concentration must have a substrate whose particular acid characteristics can tolerate the screening by part of the mobile $HSO_4^-$ without giving rise to chemical bonds, while, in turn, do not give rise to counter-screening with respect to the anion ($HSO_4^-$).

OBJECTS OF THE INVENTION

It is an object of the invention to provide a novel measuring electrode for determining the concentration of sulfuric acid solutions even at high concentration.

It is a further object of the invention to provide a method for the instantaneous determination of the charge condition of a lead-acid battery.

These and other objects and advantages of the invention will become obvious from the following detailed description.

THE INVENTION

The novel measuring electrode of the invention consists essentially of a body with at least an outer lead surface preactivated by anodic polarization in aqueous sulfuric acid. The anodic polarization is effected with a cathodically polarized counter-electrode made of any suitable corrosion resistant material such as lead, titanium or graphite. The anodic polarization in sulfuric acid is unique as anodic polarization in other electrolytes does not result in reproducible, anion sensitive electrodes. The body is preferably completely lead but the interior may be any suitable electrically conducting material.

During the anodic polarization, the lead anode becomes coated with a film of polymeric oxides with hydrogen being evolved at the cathode. Preferably, the anodic polarization is effected for 30 minutes to 60 minutes at a voltage of 3.5 to 3.9 volts at a current density of 0.6 to 0.8 A/cm². Preferably, the sulfuric acid concentration is 10 to 30% and the anodic polarization is for 30 to 60 minutes.

After this activation treatment, the lead anode is sensitive to variations of $HSO_4^-$ concentration and, when connected to a standard reference electrode such as $Hg/Hg_2Cl_2/KCl$ or $Hg/Hg_2SO_4/K_2SO_4$ and both are immersed in a sulfuric acid solution, gives rise to a variation of the electromotive force of the cell of 450 mV for an acid concentration variation of 5% to 80% and vice versa. When the acid concentration varies in the range of 10–30%, the variation in the electromotive force is 110 mV.

These activated lead electrodes, once activated, give reproducible absolute potentials and variations for long periods of time when they are kept immersed in sulfuric acid at a concentration varying from 10 to 30% and the activity of the electrodes appears to be substantially independent of the concentration of the acid in which they are kept immersed. However, the activity may decline after prolonged use and the electrodes are easily reactivated.

The reactivation treatment is similar to the pre-activation treatment but the duration of the anodic polarization is generally much shorter. Periodic re-activation permits restoration of the polymeric film of oxides on the surface of the electrode and the frequency of re-activation depends largely on the original activation treatment. For example, an electrode activated initially from 30 to 60 minutes and kept in the acid bath, loses about 10% of its activity after 24 hours and returns to its full activity after 30 seconds of re-activation treatment.

After re-activation, the electrode absolute potential corresponding to the particular concentration of the sulfuric acid electrolyte wherein it is immersed always returns to the same value and the variations of the galvanic cell potential (measuring electrode/sulfuric acid electrolyte/reference electrode) recorded for the same sulfuric acid concentration variations, coincide perfectly.

The activated measuring lead electrode of the invention appears to be specific for the $HSO_4^-$ and is not sensitive to variations of the concentrations of other anions such as $Cl^-$ or $OH^-$.

According to a preferred embodiment of the invention, the electrode is utilized for determing the charge condition of lead batteries. The measuring electrode and a suitable reference electrode are immersed in the electrolyte contained in a battery with or without an auxiliary third electrode acting as counter-electrode (cathode) during the periodic anodic re-activation of the measuring electrode. Through a suitable control circuit, the measuring electrode is anodically polarized by a push button or a reading switch with respect to the cathode of the battery or to an auxiliary counter-electrode made of graphite or other corrosion resistant cathodic material connected to the cathode of the battery for a period of time, varying from 10 to 60 seconds for example. The time can be fixed by pre-setting the time delay of a commutator-timing means incorporated into the control-circuit. This stage is to restore the measuring electrode to its full activity after a possible long period of inactivity. After this sequence, the timing means automatically commutes the measuring electrode into the measurement circuit whereby the potential between the measuring electrode and the reference electrode is detected and indicated by a suitable instrument. Since the potential, that is the acid concentration in the electrolyte of the battery, is proportional to the state of charge of the battery, the scale of the indicating instrument can be easily calibrated in percent of charge of the battery or in any other suitable form or read-out.

According to another embodiment of the invention, the measuring electrode during the periods of inactivity is subjected to a continuous small anodic polarization with respect to a counter-electrode connected to the cathode of the battery. This small but continuous anodic polarization actually keeps constant the activity of the measuring electrode. When needed, the electrode can be commutated by the actuation of a switch or of a push button to the measuring circuit for the time necessary to read the state of charge of the battery on the display instrument. Obviously, in this way, the anodic current impressed on the measuring electrode must be limited by a proper circuit in order not to effect adversely the active surface of the eletrode by excessively high and prolonged anodic polarization periods which may cause the formation of thick oxide layers no longer sensitive to $HSO_4^-$ concentration.

Referring to the FIGS.

Figure 2:
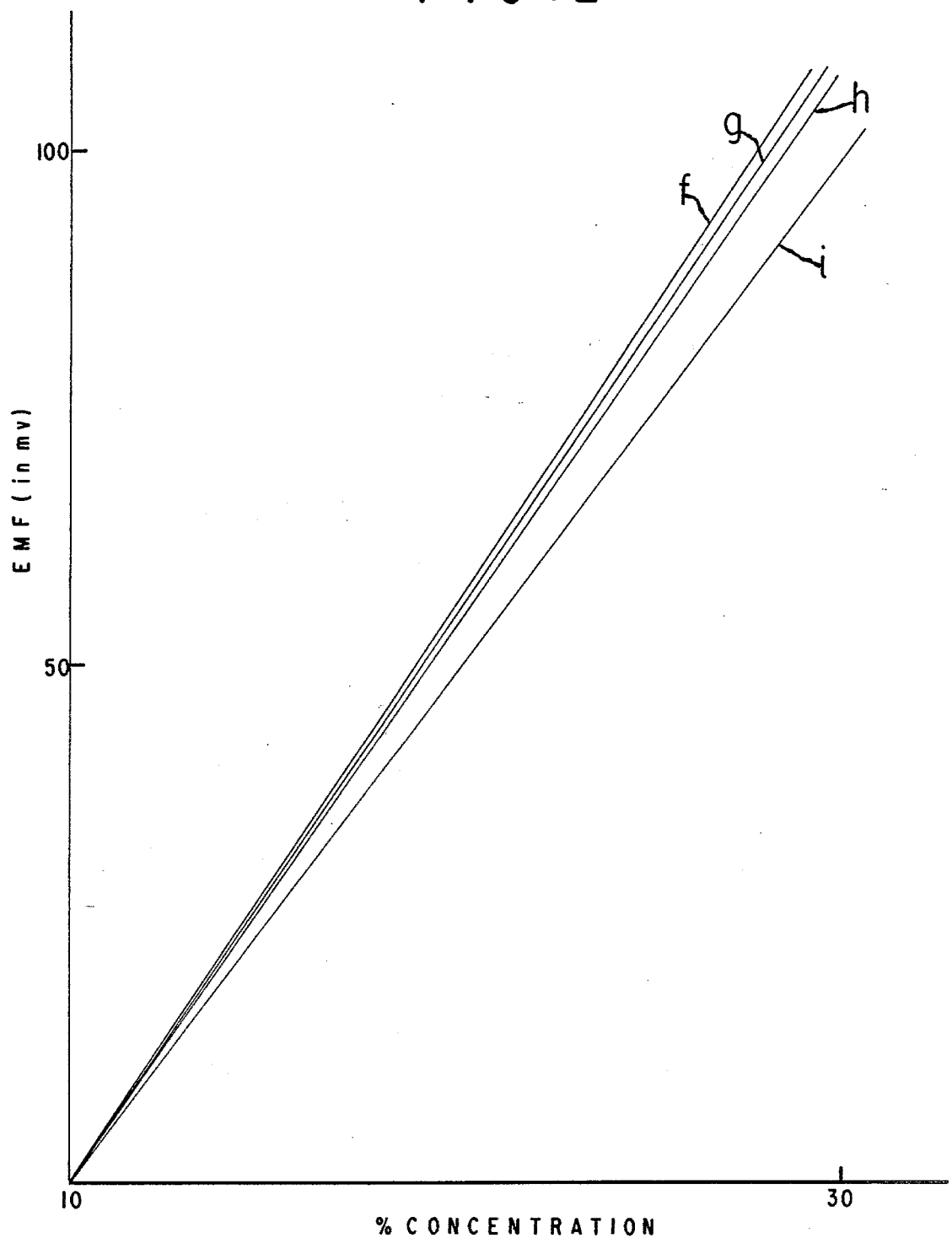

FIG. 1 illustrates the potentials readings obtained with the electrode of Example 1 and FIG. 2 illustrates the potential readings obtained with the electrode of FIG. 2.

In the following examples there are described several preferred embodiments to illustrate the invention. However, it is to be understood that the invention is not intended to be limited to the specific embodiments.

EXAMPLE 1

A lead strip measuring $10 \times 100 \times 1$ mm was connected to the positive pole of an emf generator and was subjected to anodic polarization in a 30% by weight sulfuric acid solution with a lead cathode of the same dimensions with a voltage of 3.5 volts and a current density of 0.8 $A/cm^2$. The polarization was effected at room temperature for 30 minutes. The resulting activated lead electrode was connected to a mercurous sulfate standard reference electrode and a potentiograph Metrohm model 536 to record the voltage reading. The said electrodes were immersed in sulfuric acid whose concentration was varied between 10 to 30% by weight by addition of 60% sulfuric acid and readings were taken in reverse from 30 to 10% concentration by dilution with water and the potentials were recorded. Line a of FIG. 1 in which the abscissa represents the sulfuric acid concentration in percent by weight and the ordinates are voltage variation in millivolts was recorded a variation of 100 mV.

EXAMPLE 2

An electrode prepared as in Example 1 was used without further treatment to record every hour the potential of sulfuric acid concentrations ranging from 10 to 30% by weight to obtain lines f, g and h of FIG. 2. The electrode was then immersed in 30% sulfuric acid for 24 hours and the determination of the potential of sulfuric acid was repeated with the results of line i of FIG. 2. The results obtained with the electrode which had been activated for only 30 seconds corresponds exactly to line b of FIG. 1.

EXAMPLE 3

The activation produce of Example 1 was repeated with the lead electrodes and procedures of Table I and the activated electrodes were used to obtain potential readings as in Example 1 with the reference electrodes of Table I.

sulfuric acid until it is sensitive to $HSO_4^-$ ion concentrations.

TABLE I

| | Measuring Electrode and Pre-activation Condition | | | | | | Reference Electrode Potential scan diagram of Fig. 1 | |
|---|---|---|---|---|---|---|---|---|
| Sample No. | Measuring Electrode | Counter-Electrode Cathode for activation | Voltage V | Current density A/cm² | Sulfuric acid concentration % by weight | Time in Min | | |
| 1 | lead sheet | lead | 3.5 | 0.8 | 30 | 30 | Mercurous sulfate | a,b |
| 2 | lead sheet | " | 3.3 | 0.6 | 30 | 30 | Mercurous sulfate | c |
| 3 | lead sheet | lead | 3.5 | 0.8 | 20 | 30 | Calomel | c |
| 4 | " | " | 3.5 | 0.8 | 10 | 30 | Mercurous sulfate | d |
| 5 | " | graphite | 3.9 | 0.9 | 20 | 30 | Calomel | c |
| 6 | lead rod | graphite | 3.5 | 0.6 | 10 | 20 | Calomel | d |
| 7 | " | " | 3.6 | 0.8 | 30 | 20 | Mercurous sulfate | e |

Various modifications of the electrodes and methods of the invention may be made without departing from the spirit or scope thereof and it is to be understood that the invention is to be limited only as defined in the appended claims.

We claim:

1. A measuring apparatus comprising a measuring electrode sensitive to $HSO_4^-$ ion concentrations consisting essentially of a body with at least an outer lead surface preactivated by anodic polarization in aqueous sulfuric acid electrically connected to a reference electrode for sulfuric acid for immersion of both in a lead-acid battery and means for determining the potential between the electrodes to ascertain the acid concentration.

2. A process for preparing a measuring electrode sensitive to $HSO_4^-$ ion concentrations to determine the charge of a lead-acid battery comprising subjecting an electrode with at least the outer surface being lead to anodic polarization with a counter-electrode in aqueous sulfuric acid until it is sensitive to $HSO_4^-$ ion concentrations.

3. The process of claim 2 wherein the concentration of the sulfuric acid is 10 to 30% and the polarization time is 30 to 60 minutes.

4. The process of claim 2 wherein the polarization is effected in the electrolyte of the battery whose charge is to be determined and the polarization voltage is supplied by the battery.

5. The method of claim 4 wherein the measuring electrode is reactivated every 24 hours with a 30 second polarization.

6. A method of determining the degree of charge of a lead-acid battery comprising immersing in the electrolyte of a lead-acid battery the electrodes of the apparatus of claim 1 and determining the potential of the thus formed galvanic cell.

7. The method of claim 6 wherein the electrodes are kept in the battery electrolyte and the measuring electrode is reactivated every 24 hours with a 30 second polarization.

* * * * *